United States Patent [19]

Demchak et al.

[11] 4,287,176

[45] Sep. 1, 1981

[54] ANTHELMINTIC LEVAMISOLE AND TETRAMISOLE GEL COMPOSITIONS

[75] Inventors: Richard J. Demchak, Langhorne, Pa.; Vito Corso, Jr., New Providence, N.J.

[73] Assignee: American Cyanamid Co., Stamford, Conn.

[21] Appl. No.: 195,532

[22] Filed: Oct. 9, 1980

[51] Int. Cl.³ .................... A61K 31/74; A61K 31/425
[52] U.S. Cl. ........................................ 424/78; 424/270
[58] Field of Search .................................. 424/270, 78

[56] References Cited

U.S. PATENT DOCUMENTS 4,096,262   6/1978   Andrews et al. .................... 424/270

Primary Examiner—Sam Rosen
Attorney, Agent, or Firm—H. G. Jackson

[57] ABSTRACT

The invention relates in general to aqueous, thermally revisible gels containing dl- or 1-6-phenyl-2,3,5,6-tetrahydro (−) imidazo[2,1-b]thiazole, acylamino derivatives thereof and pharmaceutically acceptable salts thereof, characterized by sub-zero gelation temperatures, storage stability and satisfactory anthelmintic activity. The invention relates in particular to gels containing levamisole, tetramisole, butamisole or benzamisole. The invention further relates to methods of use of the gels for the control of helminths infecting homothermic farm and companion animals.

11 Claims, No Drawings

ANTHELMINTIC LEVAMISOLE AND TETRAMISOLE GEL COMPOSITIONS

The invention is aqueous, thermally reversible gels containing an anthelmintic compound of formula (I)

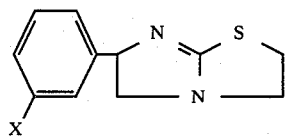

wherein X is hydrogen or —NH—R; R is $C_2$–$C_5$ alkanoyl or benzoyl, and pharmaceutically acceptable salts thereof, and the optical isomers thereof, characterized by, subzero gelation temperatures, ease of use, excellent storage stability, and satisfactory anthelmintic activity. The invention further relates to methods for the oral administration of the above gels to homothermic farm and companion animals for the control of helminths infecting same.

Among the compounds of formula (I) those preferred are levamisole, tetramisole, butamisole or benzamisole.

Helminth infections of homothermic farm and companion animals are the cause of significant economical losses in animal agriculture. Efficient control of these pests is therefore highly desirable, and can be achieved by administering to said animals an anthelmintically effective amount of levamisole, (l-6-phenyl-2,3,5,6-tetrahydroimidazo[2,1-b]thiazole), tetramisole, (dl-6-phenyl-2,3,5,6-tetrahydroimidazo[2,1-b]thiazole) butamisole, (dl-3'(2,3,5,6-tetrahydro(—)imidazo[2,1-b]thiazol-6-yl-isobutyranilide hydrochloride), benzamisole, (dl-3'-(2,3,5,6-tetrahydroimidazo[2,1-b]thiazol-6-yl-benzanilide hydrochloride or pharmaceutically acceptable salts thereof, especially the hydrochloride.

Levamisole and tetramisole may be formulated for oral administration as feed concentrates, feed additives, tablets, boluses and the like or it may be administered in the form of injectables.

Although the above delivery systems usually perform satisfactorily, some of them, such as the feed concentrates and feed additives are more suitable for large scale use and would be too expensive and/or impractical for use by the small operator. Other formulations, such as tablets, boluses, injectables and the like, though suitable for use on a small scale, are sometimes cumbersome and tedious to administer. However, gel or paste formulations may conveniently be loaded into disposable cartridges and dispersed therefrom at the required dosage rates by the use of a gun, much like the cartridge type caulking guns. The accepted temperature range for such a delivery system is −20° to +60° C., and unfortunately, the preferred gellant (U.S. Pat. No. 3,444,091 and others) for levamisole formulations has not been usable for producing systems which remain gelatinous down to −20° C.

Surprisingly we find that the novel levamisole, tetramisole, butamisole or benzamisole gel formulations of the present invention are eminently suitable for oral administration of said anthelmintics. Conveniently, these gels may be loaded into disposable cartridges and dispersed therefrom at the required dosage rates by the use of a gun, much like the cartridge type caulking guns.

The anthelmintic gels of the invention may be prepared by a plurality of procedures, such as the procedure described below:

A levamisole or tetramisole salt, preferably the hydrochloride, is dissolved in amounts of from about 3% by weight to about 15% by weight and preferably 6 to 12% by weight of formulation in deionized or distilled water used in amounts of from about 30% by weight to about 50% by weight and preferably 35% to 45% by weight of formulation. The solution is buffered by dissolving in same 1.5% by weight of citric acid and 1.0% by weight of trisodium citrate to provide a pH range at which long term chemical stability of the components is achieved, i.e. pH 3 to 3.5. Next, propylene glycol is added in amounts of from about 14% by weight to about 25% by weight of formulation.

Optional components, which may be incorporated into the above solution at this stage are:

a benzyl alcohol added in amounts of from about 0.5% by weight to about 1.5% by weight and preferably 1.5% by weight of formulation, as an antimicrobial preservative;

b the yellow dye C.I. Acid yellow No. 23; ("tartrazine"; F.D & C yellow No. 5; 4,5-dihydro-5-oxo-1-(4-sulfophenyl)-4-[(sulfophenyl)azo]-1H-pyrazole-3-carboxylic acid trisodium salt) used as coloring agent in amounts of from about 0.01% by weight to about 0.03% by weight and preferably 0.01% by weight of formulation;

c an antifoaming agent comprising a mixture of dimethylpolysiloxanes of structure:

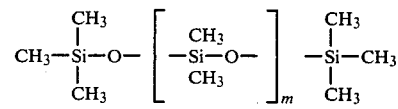

and silica gel, wherein the calculated average value of m is 200–350, the mixture is a water-white viscous oil-like liquid; d=0.965–0.970; $n_D^{25}$ about 1.404; viscosity about 60,000 centistrokes (and said antifoaming agent is described in U.S. Pat. No. 2,441,098) used in amounts of from 0.001% to 0.02% by weight and preferably 0.02% by weight of formulation.

The anthelmintic gel is prepared by cooling the above solution from about −20° C. to about −23° C. or to a subzero temperature sufficiently low for the mixture to remain fluid while the gellant is added to and dissolved in said solution. The gellant is added in amounts of from about 20% to about 30% by weight of formulation, sufficient to provide a water/gellant ratio of from 1.4/1.0 to 2.0/1.0 and preferably 1.5/1.0 to 2.0/1.0. The gellant used in these formulations is a nonionic surfactant of structure: α-hydro-Ω-hydroxy-poly(oxyethylene)poly(oxypropylene)poly(oxyethylene) block copolymer, average molecular weight 12,500; specific gravity 1.05; mp 56° C.; Brookfield viscosity 3100 at 77° C.; surface tension of a 0.1% aqueous solution: 40.6 dynes/cm at 25° C. (as measured on a du Nouy tensiometer). Finally, when all of the gellant added has dissolved, the solution is allowed to warm up and form a gel. Gels prepared by the above method and having the above composition are usually physically stable from about −20° C. to about +60° C.; i.e. within the above temperature range the formulations are gels, while outside of this range (both below and above), the formulations are liquids.

By the above method a typical gel of the invention may be prepared by dissolving 11.6 g levamisole or tetramisole hydrochloride, 1.5 g citric acid monohydrate and 1.0 g trisodium citrate dihydrate in 39.0 g of water. Next, a solution of 1.5 g of benzyl alcohol in 19.39 g of propylene glycol is added to the above aqueous levamisole solution. Then 0.01 g of the yellow dye C.I. Acid yellow No. 23 is dissolved in the above mixture. The solution is stirred and chilled to $-19°$ to $-21°$ C. and 26.0 g of the above identified gellant is added in small portions. Stirring is continued until a homogeneous solution is obtained. This solution has a gelation temperature range of from $-15°$ C. to $-18°$ C.; viscosity of the gel is $0.51 \times 10^{+6}$ cps; and the water/gellant ratio is 1.5/1.0.

Alternatively, the benzyl alcohol is added in the required amounts to the propylene glycol and the mixture stirred until solution occurs. Next, the appropriate amount of water is added and the mixture stirred until it becomes uniform. While stirring, the levamisole or tetramisole hydrochloride, citric acid and trisodium citrate are added. After all of the components dissolved the solution is filtered if necessary. The above yellow dye and the defoamer are then added, the solution is cooled to $-15°$ C. to $-10°$ C., stirred and about 75% of the appropriate gellant is added in the form of prills. The mixture is stirred until dissolution is complete, the solution is then cooled to between $-25°$ C. and $-20°$ C. and the remainder of the gellant is added (preferably in the form of a fine powder) under vacuum to remove entrapped air and other gases, and the whole is stirred until dissolution is complete. The solution is then allowed to warm up to form the desired gel.

The above procedures are equally suitable to prepare thermally reversible gels of the invention containing other anthelmintic compounds defined and described by formula (I) above.

As stated above, the thermally reversible gels of the present invention possess acceptable physical stability in a range sufficiently broad to allow their use the year around and under a variety of climatic conditions: thus, the small operator is provided with a unique tool to control helminths infecting homothermic farm and companion animals.

An additional advantage of these aqueous gel formulations is that the chemical integrity of the levamisole salts is maintained for a time period long enough to allow storage of these formulations.

As stated above, the gel compositions of the invention are well suited for the oral administration of levamisole, tetramisole and pharmaceutically acceptable salts thereof especially the hydrochloride in anthelmintically effective amounts of from about 3 mg to 10 mg/kg body weight and preferably 6–8 mg/kg body weight to homothermic form and companion animals for the control of helminths infecting same.

EXAMPLE 1

Preparation of levamisole gels

General Procedure

The appropriate amounts of levamisole salt such as the hydrochloride, citric acid monohydrate and trisodium citrate dihydrate are dissolved in deionized or distilled water and the solution clarified if necessary. Next, the required amount of propylene glycol is added to the above solution.

If benzyl alcohol is used as an antimicrobial preservative in any one of the formulations, then it is of advantage to dissolve same in the propylene glycol before the glycol is added to the above aqueous solution.

If so desired, a small amount of a yellow dye (C.I. Acid yellow No. 23) may be added to the above solution. Similarly, an antifoaming agent may also be added to the above solution at this point, if so desired. Said antifoaming agent is a mixture of dimethylpolysiloxanes of formula:

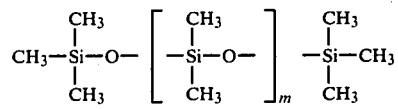

and of silica gel, wherein the calculated average value of m is from 200 to 350; the mixture is a water-white, viscous, oil-like liquid: $d=0.965-0.970$; $n_D^{25}$ about 1.404; viscosity at $25°$ C. is about 60,000 centistokes.

The thus prepared homogeneous solution is then chilled to a sub-zero temperature, selected to be in a range sufficiently low to prevent the premature formation of a gel while the gellant is added and dissolved in the solution. The gellant selected is a nonionic surfactant of structure: α-hydro-Ω-hydroxy-poly(oxyethylene)poly(oxypropylene)poly(oxyethylene) block copolymer, average molecular weight 12,500; mp 56° C.; Brookfield viscosity of 3100 at 77° C.; surface tension of a 0.1% aqueous solution: 40.6 dynes/cm (measured with a du Nouy tensiometer).

The thus prepared formulations are then equilibrated at various temperatures in a cold bath to determine their gelation temperature range. Brookfield viscosities are determined with a Synchro-Lectric RV viscometer, using a T-F spindle at 5 r.p.m.

The composition of the formulations and other data obtained are summarized in Table I below.

TABLE I

Composition and physical parameters of various levamisole gels

| Component | Percent by weight Composition of formulations | | | | | |
|---|---|---|---|---|---|---|
| | No. 1 | No. 2 | No. 3 | No. 4 | No. 5 | No. 6 |
| Levamisole . HCl | 10.49 | 12.00 | 11.60 | 11.60 | 11.60 | 11.73 |
| Water | 50.00 | 45.00 | 45.00 | 40.00 | 39.00 | 37.50 |
| Gellant | 20.00 | 20.00 | 25.00 | 25.00 | 26.00 | 25.00 |
| Citric Acid Monohydrate | 1.50 | 1.50 | 1.50 | 1.50 | 1.50 | 1.50 |
| Trisodium citrate, dihydrate | 1.00 | 1.00 | 1.00 | 1.00 | 1.00 | 1.00 |
| Benzyl alcohol | — | — | 1.50 | 1.50 | 1.50 | 1.50 |
| C.I. Acid yellow No. 23 | 0.01 | 0.01 | 0.01 | 0.01 | 0.01 | 0.01 |
| Antifoaming Agent | — | — | — | — | — | 0.02 |
| Propylene glycol | 17.00 | 20.49 | 14.39 | 19.39 | 19.39 | 21.74 |
| Total | 100.00 | 100.00 | 100.00 | 100.00 | 100.00 | 100.00 |
| Water/gellant Ratio | 2.5/1.0 | 2.25/1.0 | 1.8/1.0 | 1.6/1.0 | 1.5/1.0 | 1.5/1.0 |
| gelation temperature °C. | +11 to +13 | +6 to +10 | −7 to −9 | −11 to −14 | −15 to −18 | −15 to −18 |

TABLE I-continued

Composition and physical parameters of various levamisole gels

| Component | Percent by weight Composition of formulations | | | | | |
|---|---|---|---|---|---|---|
| | No. 1 | No. 2 | No. 3 | No. 4 | No. 5 | No. 6 |
| viscosity, cps × $10^{-6}$ | 0.33 | — | — | — | 0.51 | 0.66 |

EXAMPLE 2

Evaluation of the thermal stability of an unbuffered levamisole gel formulation

An unbuffered aqueous gel is prepared by the procedure of Example 1, comprising: approximately 6.7% by weight of levamisole hydrochloride, 0.01% by weight of C.I. Acid yellow No. 23 (F.D & C yellow dye No. 5), 55% by weight of deionized water, 22% by weight of gellant (the gellant of Example 1) and propylene glycol to q.s. ad 100%.

Samples of the above gel are stored at 0° C., room temperature, 37° C. and 45° C. both in polyethylene and glass bottles for a period of time of three months and are analyzed at one month intervals. The data obtained are summarized in Table II below, wherein it can be seen that even in an unbuffered gel very little levamisole is lost from a sample stored for 3 months at 45° C.

TABLE II

Evaluation of the thermal stability of a levamisole gel

| Time | Container | Percent levamisole present 28 temperature | | | |
|---|---|---|---|---|---|
| | | 0° C. | RT | 37° C. | 45° C. |
| Initial | | 6.69 | 6.69 | 6.69 | 6.69 |
| 1 month | polyethylene | 6.68 | 6.66 | 6.62 | 6.59 |
| | glass | 6.70 | — | — | 6.49 |
| 2 month | polyethylene | 6.56 | 6.59 | 6.48 | 6.49 |
| | glass | 6.65 | — | — | 6.54 |
| 3 month | polyethylene | 6.56 | 6.59 | 6.45 | 6.38 |
| | glass | 6.62 | — | — | 6.36 |

EXAMPLE 3

Preparation of thermally reversible levamisole gels which are characterized by sub-zero gelation temperatures Following the procedure of Example 1, the appropriate amounts of levamisole hydrochloride, citric acid monohydrate and trisodium citrate dihydrate are dissolved in deionized or distilled water. Sufficient amounts of the buffering agents are used to provide the finished gel with a pH in the range of from pH 3.0 to pH 3.5, benzyl alcohol is then dissolved in the propylene glycol and the mixture added to the levamisole solution. The thus prepared homogenous solution is then chilled to a temperature between about −20° C. and −25° C. and a sufficient amount of the gellant, α-hydro-Ω-hydroxypoly(oxyethylene)poly(oxypropylene)poly(oxyethylene) block copolymer (average molecular weight 12,500; specific gravity 1.05; mp 56° C., added to said homogeneous solution to provide a water/gellant ratio of from 1.4/1.0 to 2.0/1.0. The gel compositions thus prepared are thermally reversible and are characterized by sub-zero gelation temperatures.

TABLE III

| Component | Percent by weight composition of formulation | |
|---|---|---|
| levamisole hydrochloride | 3.0 | 15.0 |
| (tech) | | |
| Gellant | 23.5 | 23.0 |
| Water | 44.65 | 43.70 |
| Citric Acid | 1.50 | 1.50 |
| Trisodium Citrate | 1.00 | 1.00 |
| Benzyl alcohol | 1.50 | 1.50 |
| Propylene glycol | 24.85 | 14.30 |
| Total | 100.00 | 100.00 |
| Water/gellant ratio | 1.9/1 | 1.9/1 |
| Gelation temperature °C. | −7 to −9 | −3 to −5 |

EXAMPLE 4

Determination of Levamisole blood levels in Cattle treated with a levamisole gel Crossbred steers weighing between 175 and 225 kg are randomly distributed into three groups of three animals each. While being tested, the animals are daily offered grass hay, silage and water ad libitum.

One group is dosed orally with levamisole oblets at the rate of 8 mg levamisole.HCl/kg body weight;

One group is dosed orally with levamisole.HCl paste at the rate of 8 mg levamisole.HCl/kg body weight; and One group is dosed orally with a levamisole.HCl gel (prepared by the method of Example 1, No. 4) at the rate of 8 mg/kg body weight.

Blood samples are taken at regular intervals posttreatment and the level of levamisole in the blood determined. The data thus obtained are averaged and are summarized in Table IV below.

TABLE IV

Levamisole . HCl levels in Cattle blood

| Levamisole Formulations | Levamisole HCl (ppm) in Blood at Hours Posttreatment | | | | | | |
|---|---|---|---|---|---|---|---|
| | 0.5 | 1 | 2 | 3 | 4 | 6 | 8 |
| Gel | 0.99 | 0.96 | 0.81 | 0.65 | 0.61 | 0.50 | 0.37 |
| Paste | 0.41 | 0.42 | 0.49 | 0.46 | 0.39 | 0.34 | 0.20 |
| OBLET | 0.81 | 0.79 | 0.64 | 0.53 | 0.44 | 0.34 | 0.28 |

It can be seen from the above table that the anthelmintic enters and is maintained in the animals circulatory system at a much higher level for a prolonged period of time when administered orally from a gel of the invention rather than via an oblet or paste.

We claim:

1. An aqueous composition comprising: 3% to 15% by weight of a pharmaceutically acceptable salt of the anthelmintic compound of the formula:

(dl)

wherein X is hydrogen or —NH—R; R is C₂–C₅ alkanoyl or benzoyl; or the optical isomers thereof; 30% to 50% by weight of water; 1.5% by weight of citric acid; 1.0% by weight of trisodium citrate acid; 14% to 25% by weight of propylene glycol; and 20% to 30% by weight of the gellant α-hydro-Ω-hydroxy-poly(oxyethylene)poly(oxypropylene)poly(oxyethylene) block copolymer, average molecular weight 12,500, specific gravity 1.05; mp 56° C., viscosity 3100 at 77° C.; wherein said compositions are gels in the temperature range of from −20° C. to +60° C.; with the provisos that the water/gellant ratio is from 1.4/1.0 to 2.0/1.0; and that the components of said composition add up to a total of 100% by weight.

2. An aqueous composition comprising: 3% to 15% by weight of a pharmaceutically acceptable salt of the anthelmintic 1-6-phenyl-2,3,5,6-tetrahydroimidazo-[2,1-b]thiazole or dl-6-phenyl-2,3,5,6-tetrahydroimidazo-[2,1-b]thiazole; 30% to 50% by weight of water; 1.5% by weight of citric acid; 1.0% by weight of trisodium citrate acid; 14% to 25% by weight of propylene glycol; and 20% to 30% by weight of the gellant α-hydro-Ω-hydroxy-poly(oxyethylene)poly(oxypropylene)poly(oxyethylene) block copolymer, average molecular weight 12,500, specific gravity 1.05; mp 56° C., viscosity 3100 at 77° C.; wherein said compositions are gels in the temperature range of from −20° C. to +60° C.; with the provisos that the water/gellant ratio is from 1.4/1.0 to 2.0/1.0; and that the components of said composition add up to a total of 100% by weight.

3. An aqueous, thermally reversible gel composition characterized by a sub-zero gelation temperature, comprising: 3% to 15% by weight of a pharmaceutically acceptable salt of the anthelmintic 1-6-phenyl-2,3,5,6-tetrahydroimidazo[2,1-b]thiazole or dl-6-phenyl-2,3,5,6-tetrahydroimidazo[2,1-b]thiazole; 14% to 25% by weight of propylene glycol; an antimicrobially effective amount of benzyl alcohol; at least 30% by weight of water; at least 20% by weight of the gellant α-hydro-Ω-hydroxypoly(oxyethylene)poly(oxypropylene)poly(oxyethylene) block copolymer which has an average molecular weight of 12,500 and a specific gravity of 1.05 and provided that the ratio of water to gellant is in the range of from 1.4/1.0 to 2.0/1.0; and a sufficient amount of a buffer to adjust the pH of the finished gel composition to between pH 3.0 and pH 3.5.

4. A composition according to claim 2, comprising: 6% to 12% by weight of said anthelmintic; 35% to 45% by weight of water; 1.5% by weight of citric acid; 1.0% by weight of trisodium citrate; 14% to 25% by weight of propylene glycol; 20% to 30% by weight of said gellant; 0.5% to 1.5% by weight of benzyl alcohol; 0.01% to 0.03% by weight of C.I. Acid yellow No. 23; 0.001% to 0.02% by weight of an antifoaming agent comprising a mixture of dimethylpolysiloxanes of formula:

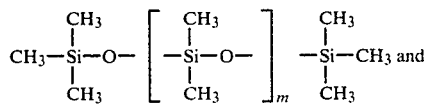

silica gel wherein the calculated average value of m is 200–350, the mixture is a viscous liquid, d=0.965–0.970, $n_D^{25}$ about 1.404, viscosity about 60,000 centistokes; with the proviso that the water/gellant ratio is from 1.5/1.0 to 2.0/1.0.

5. A composition according to claim 4, comprising: 11.73%; by weight of the hydrochloride of said anthelmintic; 37.5% by weight of water; 1.5% by weight of citric acid; 1.0% by weight of trisodium citrate; 21.74% by weight of propylene glycol; 25% by weight of said gellant; 1.5% by weight of benzyl alcohol; 0.01% by weight of C.I. Acid yellow No. 23; and 0.02% by weight of said antifoaming agent.

6. A composition according to claim 2, wherein the anthelmintic is 1-6-phenyl-2,3,5,6-tetrahydroimidazo[2,1-b]thiazole.

7. A method for the preparation of an aqueous thermally reversible composition, characterized by a sub-zero gelation temperature, comprising: dissolving 3% to 15% by weight of a pharmaceutically acceptable salt of the anthelmintic compound of formula:

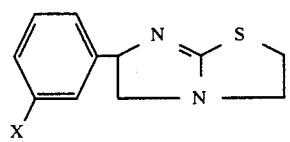

wherein X is hydrogen or —NH—R; R is C₂–C₅ alkanoyl or benzoyl; or the optical isomers thereof; 1.5% by weight of citric acid and 1.0% by weight of trisodium citrate in 30% to 50% by weight of water; dissolving 0.5% by weight of benzyl alcohol in 14% to 25% by weight of propylene glycol; combining the two solutions and adding 0.01% to 0.03% by weight of C.I. Acid yellow No. 23; 0.001% to 0.02% by weight of an antifoaming agent comprising a mixture of dimethylpolysiloxanes of formula:

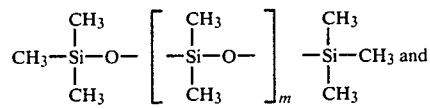

silica gel wherein the calculated average value of m is 200–350, the mixture is a viscous liquid, d=0.965–0.970, $n_D^{25}$ about 1.404, viscosity about 60,000 centistokes; stirring and cooling the combined solution mixture from −20° C. to −22° C. and adding 20% to 30% by weight of the gellant α-hydro-Ω-hydroxy-poly(oxyethylene)poly(oxypropylene)poly(oxyethylene) block copolymer, average molecular weight 12,500; specific gravity 1.05; mp 56° C., viscosity 3100 at 77° C.; and stirring said mixture until a clear solution occurs; with the provisos that the water/gellant ratio is from 1.4/1.0 to 2.0/1.0; and that the components of said composition add up to a total of 100%.

8. A method for the preparation of an aqueous thermally reversible composition, characterized by a sub-zero gelation temperature, comprising: dissolving 3% to 15% by weight of a pharmaceutically acceptable salt of the anthelmintic 1-6-phenyl-2,3,5,6-tetrahydroimidazo[2,1-b]-thiazole, or dl-6-phenyl-2,3,5,6-tetrahydroimidazo[2,1-b]-thiazole; 1.5% by weight of citric acid and 1.0% by weight of trisodium citrate in 30% to 50% by weight of water; dissolving 0.5% to 1.5% by weight of benzyl alcohol in 14% to 25% by weight of propylene glycol; combining the two solutions and adding 0.01% to 0.03% by weight of C.I. Acid yellow No. 23; 0.001% to 0.02% by weight of an antifoaming agent comprising a mixture of dimethylpolysiloxanes of formula

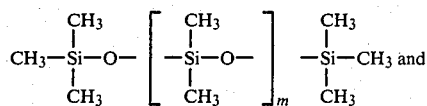

silica gel wherein the calculated average value of m is 200–350, the mixture is a viscous liquid, d=0.965–0.970, $n_D^{25}$ about 1.404, viscosity about 60,000 centistokes; stirring and cooling the combined solution mixture from −20° C. to −22° C. and adding 20% to 30% by weight of the gellant α-hydro-Ω-hydroxy-poly(oxyethylene)-poly(oxypropylene)poly(oxyethylene) block copolymer, average molecular weight 12,500, specific gravity 1.05; mp 56° C., viscosity 3100 at 77° C.; and stirring said mixture until a clear solution occurs; with the provisos that the water/gellant ratio is from 1.4/1.0 to 2.0/1.0; and that the components of said composition add up to a total of 100%.

9. A method for the control of helminths, comprising: administering orally to homothermic farm and companion animals a composition according to claim 1, to provide said animals with the anthelmintic in amounts of from 3 mg to 10 mg/kg body weight, per dosage.

10. A method according to claim 9 wherein the anthelmintic is tetramisole.

11. A method according to claim 9 wherein the anthelmintic is levamisole.

* * * * *